(12) United States Patent
Kennedy

(10) Patent No.: US 7,964,409 B1
(45) Date of Patent: Jun. 21, 2011

(54) DETECTING HYPOCALCEMIA USING BOVINE NOSE SWEAT

(75) Inventor: Gary A. Kennedy, Ruston, LA (US)

(73) Assignee: Louisiana Tech Research Foundation; a Division of Louisiana Tech University Foundation, inc., Ruston, LA (US)

( * ) Notice: Subject to any disclaimer, the term of this patent is extended or adjusted under 35 U.S.C. 154(b) by 506 days.

(21) Appl. No.: 12/027,076

(22) Filed: Feb. 6, 2008

Related U.S. Application Data

(60) Provisional application No. 60/889,879, filed on Feb. 14, 2007, provisional application No. 60/888,595, filed on Feb. 7, 2007.

(51) Int. Cl.
*G01N 33/20* (2006.01)

(52) U.S. Cl. ............ 436/79; 436/74; 436/164; 436/805; 436/811; 436/815

(58) Field of Classification Search ............... 436/74, 436/79, 164, 805, 807, 811, 815
See application file for complete search history.

(56) References Cited

U.S. PATENT DOCUMENTS

| | | | |
|---|---|---|---|
| 4,761,369 A | 8/1988 | Steinman | |
| 4,795,712 A * | 1/1989 | Toner et al. | 436/74 |
| 5,262,330 A | 11/1993 | Chapoteau et al. | |
| 5,629,211 A * | 5/1997 | Tsutsumi | 436/74 |
| 6,994,973 B2 * | 2/2006 | Krenn et al. | 435/6 |

OTHER PUBLICATIONS

Matsas, David J., Warnick, Lorin D., Mechor, Gerald D., Seib, Laverne N., Patone, Sandra, White, Maurice E., Guard, Charles L., "Use of a Water Hardness Test Kit to Measure Serum Calcium Concentration in Cattle," JAVMA, vol. 214, No. 6, Mar. 15, 1999, pp. 826-828.

Elsa M. Janle, Ph.D., Interstitial Fluid Calcium, Magnesium and Phosphorus Concentrations in Bone, Muscle and Subcutaneous Tissue Sampled with Ultrafiltration Probes, Current Separations, 2001, pp. 81-85, 19:3.

* cited by examiner

*Primary Examiner* — Jill Warden
*Assistant Examiner* — Monique Cole
(74) *Attorney, Agent, or Firm* — Jones, Walker, Waecheter, Poitevent, Carrere & Denegre, LLP

(57) ABSTRACT

The invention is collecting nose sweat and testing the nose sweat for levels of calcium. Testing may be done using standard laboratory procedures for calcium detection, or may be done cow-side using a suitable test for calcium levels, such as a water hardness test kit or a suitable test strip.

17 Claims, 2 Drawing Sheets

Total calcium concentrations measured from blood and nose sweat samples

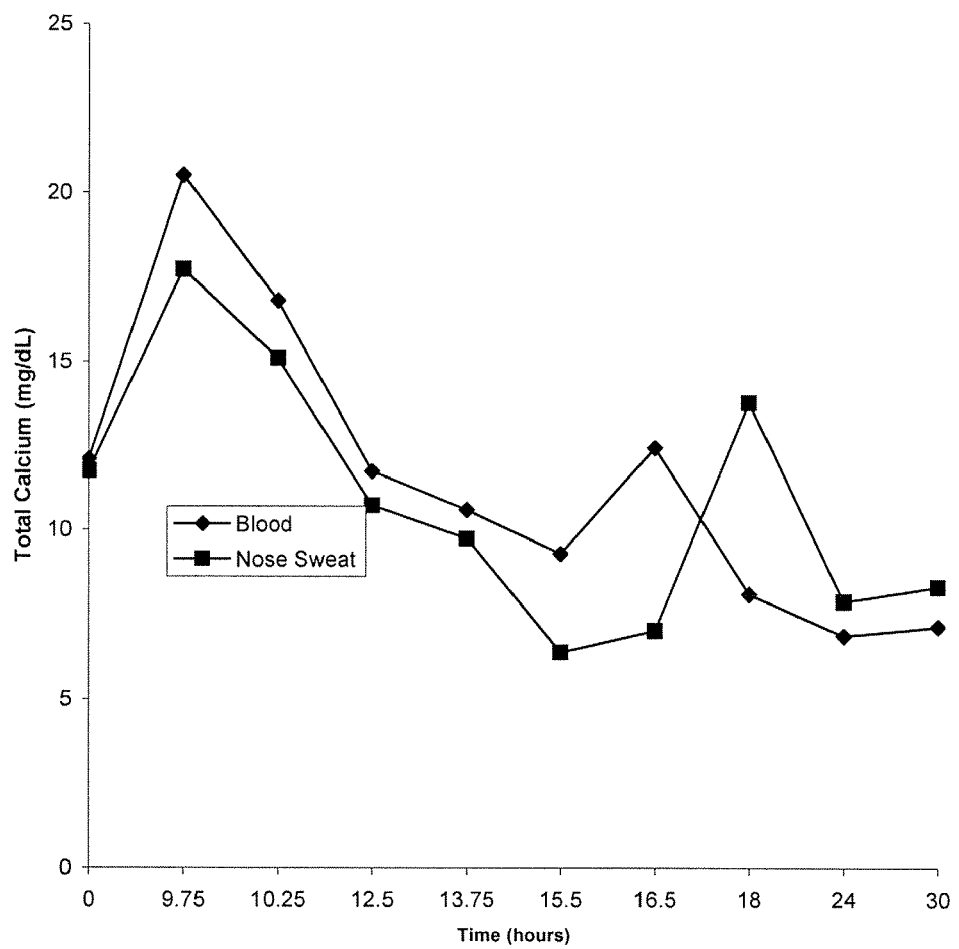
Figure 1. Total calcium concentrations measured from blood and nose sweat samples

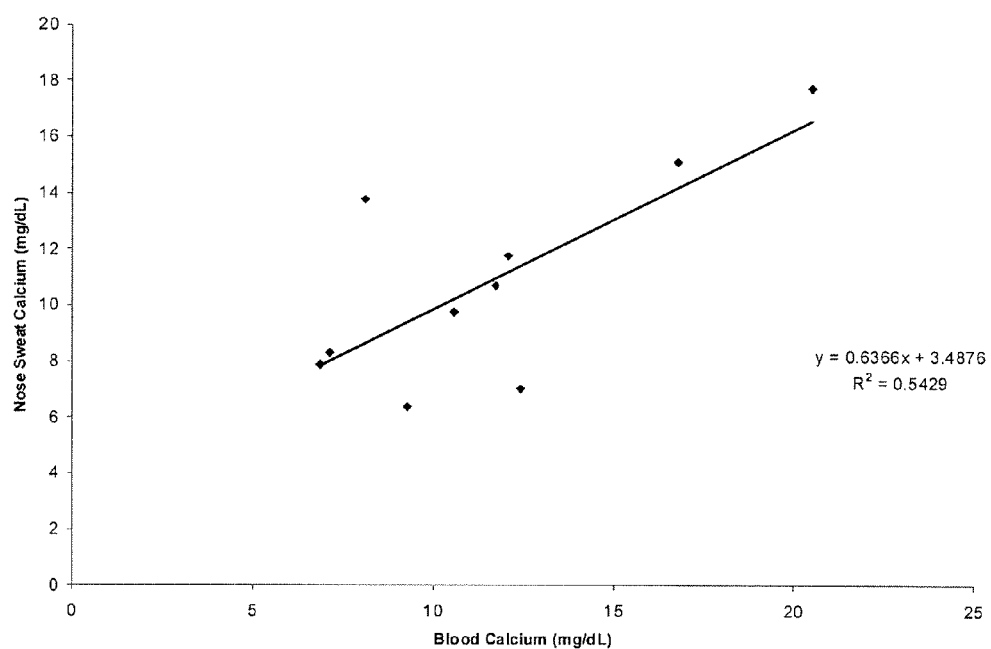
Figure 2. Regression line and equation estimated from blood and nose sweat data.

DETECTING HYPOCALCEMIA USING BOVINE NOSE SWEAT

PRIORITY CLAIM

This application claims the priority benefit of U.S. provisional applications 60/889,879, filed on Feb. 14, 2007; and 60/888,595 filed on Feb. 7, 2007, and both applications are incorporated here by reference.

FIELD OF INVENTION

This invention relates to methods of testing cattle for calcium level, and in particularly using readily available body fluids, in particular, nose sweat.

BACKGROUND OF THE INVENTION

The U.S. dairy industry is largely comprised of farmer-owned dairy cooperatives and proprietary companies. The cooperatives tend to specialize in fresh milk and butter where proprietary companies control branded cheeses and cultured products. Through the use of technology, the dairy industry has increased milk production over the past 10 years. The number of dairy operations has declined while per animal efficiency has increased. Due to intense milking schedules and loss of nutrients involved with the milking process, health problems for dairy cows have been compounded. This ultimately costs dairy producers, which in turn costs dairy consumers. Early detection of health problems in dairy cattle could prevent death loss and financial burdens on the dairy industry.

A common problem in dairy cattle is hypocalcemia or "milk fever." Milk fever in dairy cows results from an acute deficiency of blood calcium which typically occurs in the time immediately before calving. While the problem exists in all cows, it is more acute in dairy cattle. It has been reported that the average incidence of milk fever is about 6% in U.S. dairy herds, although it may be much higher on individual farms (Sanchez et al., 1992). Calving causes a high volume of milk production, and with it, a high demand for calcium from the cow's body. If the body is unable to respond quickly to this demand, the cow develops hypocalcemia, or an abnormally low blood-calcium level. Hypocalcemic cows will begin trembling and, as calcium level continues to plummet, will no longer be able to stand. Left untreated, most affected cows will die. Shortly before calving, large amounts of calcium are removed from the blood and are utilized in the mammary gland to be part of the colostrum, defined as milk that is secreted for a few days after parturition and characterized by high protein and antibody content. Calcium in the colostrum may be 8 to 10 times greater than that in the blood supply. The rapid drop and the decreased mass of the calcium pool prior to parturition, and the failure of calcium absorption to increase fast enough after the onset of lactation, can predispose animals to hypocalcemia. A cow afflicted with acute milk fever may remain alert, eat, and milk, but is not able to stand. The cow may become a "creeping downer" that has flexed pasterns and posterior paralysis. The condition can lead to rupture of the large muscle or group of muscles in one or both of the hind legs. In this downer condition, the cow is also susceptible to fracture or dislocation of a hind joint when the cow initially goes down or struggles to rise, as well as possible damage to the udder which can lead to mastitis.

Milk fever can also result in lost milk production, poor reproductive performance, increased culling rates, additional labor costs to treat afflicted animals, and animal death. Subacute milk fever causes cows to be easily excited, with symptoms of muscle twitching and tremors. The onset of milk fever causes notable changes in the blood parameters, especially blood calcium. Normal blood calcium (total calcium levels) in an adult dairy cow generally ranges from 8-10 mg per dl. In stage one hypocalcemic cows, blood calcium levels range from 5.5 to 7.5 mg per dl. Stage two hypocalcemia is characterized by blood calcium levels of 3.5 to 6.5 mg per dl. In stage three, calcium levels may drop as low as 2.0 mg per dl. The drop in blood calcium levels is usually accompanied by a drop in phosphorus concentrations and an increase in magnesium concentration (Smith, 1996).

Traditional tests for calcium levels involve testing blood serum. This requires taking a blood sample from the "patient," and running that sample through a standard test to determine the complete calcium level in the sample. Essentially all of the calcium found in blood is present in the plasma as two distinct forms: nondiffusible protein-bound calcium (bound to albumin, for instance) and the diffusible free calcium fraction. Of the two forms, the nondiffusible protein-bound fraction constitutes roughly 40% to 50% of the total extracellular calcium, while the diffusible free fraction can be further subdivided into ionized calcium (which is the physiologically active form) and complexed calcium (which is found bound to bicarbonate, citrate, phosphate, and sulfate).

The usual calcium level test determines the total calcium levels (both diffusible and non-diffusible calcium), as testing for ionic calcium is a more burdensome test. The total calcium test is a good reflection of the amount of free calcium involved in metabolism since the balance between free and bound is usually stable and predictable. Methods to test a blood serum sample for total calcium include atomic absorption spectrophotometry analysis, oxalate precipitation followed by titration, fluorometric, titrimetric, flame photometry and photometric determination (as exemplified in U.S. Pat. No. 4,871,678, or descried in Gindler E M, King J D. Rapid Colorimetric Determination of Calcium in Biologic Fluids with Methylthymol Blue. Am J Clin Path 1972; 58:376-382. 22). Photometric determination involves the use of dye complexes (such as methylxyenol blue, arsenazo III or o-cresolphthalein complexone) that reacts with calcium in a particular environment (acidic, buffered, etc) yielding a colored calcium-dye complex. The resulting increase in absorbance caused by the formation of the complex is bichromatically measured (such as by spectrophotometric means) and correlated to the calcium concentration of the sample. See, in general, Burtis and Ashwood, *Tietz Textbook of Clinical Chemistry*, $2^{nd}$ Ed, W. B. Saunders 1994, chap 36, hereby incorporated by reference, which describes several of the methods above. Due to the importance of calcium in biological systems, the attention paid to determining calcium levels is reflected in a number of patents addressing the issue, such as U.S. Pat. No. 5,618,684 (Method of determination of calcium); U.S. Pat. No. 5,482,866 (Method for quantization of calcium and magnesium and the novel reagent compositions); U.S. Pat. No. 5,262,330 (Colorimetric methods and reagents for the assay of calcium in a test); U.S. Pat. No. 5,057,435 (Reagent and methods for calcium determination); U.S. Pat. No. 4,795,712 (Calcium complexing dyes and their use in analytical compositions, elements and methods).

While serum calcium levels will reveal calcium levels which are used to diagnose hypocalcemia, treatment is usually initiated based on clinical signs only (i.e., often at advanced stages of the condition) because of the slow return of laboratory blood tests and the rapid nature of this illness. Affected cows have an excellent prognosis if the condition is diagnosed and treated early and properly. Late diagnosis and delayed treatment may result in a comatose animal with a much poorer prognosis. If treatment is not successful, death of the animal results. Animal survival is favorable with early treatment by intravenous calcium supplementation. However, repeated treatments with intravenous calcium can suppress homeostatic mechanisms for increasing serum calcium (Smith, 1996), suppressing the animal's normal mechanism for regulating serum calcium thereby compounding the problem. Consequently, the need for repeated treatment should be based on laboratory verification of low serum calcium levels. Treatment costs for milk fever are estimated to be about $334 per head (Smith, 2002).

Treatment for milk fever has been estimated to cost the dairy industry $167 million annually (excluding death loss). Other than the current blood serum tests, the dairy industry has no proven technique for accurately measuring calcium levels. Blood serum tests, if undertaken at all, are typically "too little, too late" for the animal and the dairy. By the time symptoms are present, milk production has already been significantly affected and the animal is in danger. The ability to monitor bovine blood calcium concentrations in real-time without any disease indicator would be beneficial in possibly preventing, diagnosing, and/or treating hypocalcemia.

The basic problem is that traditional tests for calcium levels in cows require a blood sample, and as the sample must be sent to a lab for analysis, traditional methods entail a delay in results, coupled with a costly test. Proper handling of the blood sample is problematic, requiring cooling and centrifugation to produce blood plasma or serum. In addition, the collection of blood specimens from the jugular vein, the anterior mammary (milk) vein, or the coccygeal grove at the top of the tail head would require frequent animal venipuncture. This could result in undesirable animal behavior, increased animal stress, and reduced milk production. It would be advantageous to avoid taking a blood sample, and further to have an efficient and easily administered means for monitoring calcium concentrations in the animal, preferably at "cow-side" before symptoms develop or advance so the appropriate measures, such as administration of subcutaneous, intraperitoneal, oral, or intravenous calcium products, can be taken to avoid or early-treat milk fever. An alternative method of monitoring blood calcium levels may be possible, provided that there is a correlation between blood calcium concentrations and calcium concentrations in other body fluids that may be readily accessed without venipuncture.

SUMMARY OF THE INVENTION

The invention is collecting nose sweat and testing the nose sweat for levels of calcium. Testing may be done using standard laboratory procedures for calcium detection, or may be done cow-side using a suitable test for calcium levels, such as a water hardness test kit or a suitable test strip,

BRIEF DESCRIPTION OF THE FIGURES

FIG. 1 is a graph of nose sweat calcium levels and blood serum calcium levels versus time after giving a calcium injection.

FIG. 2 is a graph showing the MMSE regression line on the cross-plot of blood versus nose calcium levels.

DESCRIPTION OF THE PREFERRED EMBODIMENT

The invention entails testing bovine nose fluids (nose sweat) for calcium levels. After testing, the nose sweat calcium level can be correlated against predetermined thresholds indicating disease.

A needed precursor to an effective treatment is to find a proxy body fluid that could be easily obtained in the field and was a reliable indicator of blood calcium levels, and hopefully, field testable for calcium levels. Prior studies indicated that calcium concentrations in plasma, bone, muscle, and subcutaneous interstitial space in sheep demonstrated no significant difference in calcium among bone, muscle and subcutaneous tissues, but there were significant difference between blood calcium and the former tissues (Janle et al., 2001).

We studied a readily available bovine body fluid, nose sweat, and compared it with blood calcium concentrations to determine if the calcium levels in nose sweat correlated with that of blood in a reliable and repeatable manner. The bovine sweat gland is located in the nose of the animal and nose sweat are readily obtained, such as with a swab. Nose sweat was obtained from a Jersey dairy cow by obtaining sweat from the exterior surface of the nose, substantially free from mucous. Baseline samples of nose sweat and blood were drawn approximately eight hours prior to administering 500 ml of CMPK intravenously.

The sweat fluid that collects on the nose was collected for analysis. This procedure involved rinsing the nose with deionized water and wiping it dry with a clean cotton cloth. Sweat was allowed to recollect on the nose and was then gently scraped into a container and subsequently transferred by syringe into a microcentrifuge tube. This procedure was repeated until 1 microliter of sweat had been collected. The samples were then frozen and stored for analysis. Baseline samples of nose sweat and blood drawn from the jugular vein were collected approximately eight hours prior to administration of 500 ml of CMPK intravenously. Corresponding nose sweat and blood samples were collected periodically over a 30-hour time period following the CMPK administration. After all samples were collected, analytical calcium measurements were performed using standard analytical optical techniques. Total calcium levels of both blood and sweat were determined by spectrophotometric analysis of blood plasma and the nose sweat using o-cresolphthalein complexone as the complexing dye. The data collected from this experiment are presented in Table 1 and the results are illustrated in FIG. 1. The data presented in Table 1 and illustrated in FIG. 1 represent total serum calcium levels.

TABLE 1

Data from blood and nose sweat samples collected

| Time Period (Hours) | Blood Calcium (mg/dL) | Nose Sweat Calcium (mg/dL) |
| --- | --- | --- |
| 0.00 | 12.10 (baseline) | 11.76 (baseline) |
| 8.00 | intravenous infusion of 500 ml CMPK | |
| 9.75 | 20.53 | 17.74 |
| 10.25 | 16.80 | 15.10 |
| 12.50 | 11.74 | 10.72 |
| 13.75 | 10.59 | 9.75 |
| 15.50 | 9.29 | 6.39 |
| 16.50 | 12.44 | 7.03 |
| 18.00 | 8.10 | 13.78 |
| 24.00 | 6.87 | 7.88 |

As can be seen from FIG. 1, the blood and nose fluid calcium levels rise and fall with the infusion of calcium, demonstrating a strong correlation between the two tissues. A regression on the data results in highly significant p-value of 0.013 for the slope coefficient and an R-square (0.54), typical for this type of data (see FIG. 2). The nose fluid and blood samples had a correlation of +0.74.6. The best fit regression equation results in the following regression equation:

Nose sweat total calcium level=0.6366(blood plasma total calcium level)+3.4875, or (with rounding) or Blood=(nose−3.49)*1.57;

this equation will be refined with the inclusion of a larger experimental data set.

From this good fit of this regression, we see that nose sweat can be used as a surrogate for blood. We estimate nose sweat calcium levels with blood fluid levels for relevant indicators as follows;

| Total Calcium Indicator | | |
|---|---|---|
| Blood Level | Nose Level | Indicator |
| 8-10 mg/dL | 8.5-9.9 mg/dl | normal levels |

As 1 mg/dl is equivalent to 10 ppm, the indicator can be measured in using either ppm or mg/dL criteria.

The above ranges are approximations for the calcium blood and will vary from animal to animal. It is appropriate to say that total calcium blood levels below 8 mg/dL (80 ppm) are probative of the animal's health being in jeopardy. Levels at or above 85 ppm are generally probative of a contra indicator of milk fever. For instance, nose measured levels of below 8.0 mg/dl (or 800 ppm) may be used as an indicator that the animal may have milk fever, and needs to be closely monitored. Nose level readings substantially below this level (say nose calcium levels of about 70 ppm or below) may be used as an indicator to undertake actual blood serum measurements to determine the stage of the disease. Further, it has been observed that a precipitous drop in calcium levels in the blood is accompanied by the more serious effects of milk fever. If a suspect animal is closely monitored (e.g. using nose sweat to monitor on a daily basis) this rapid drop can be detected by a corresponding rapid change in nose measured calcium levels, and corrective action taken.

As can be seen, the total calcium levels in bovine nose sweat may be used as an indicator of calcium related diseases. In the most general form, the invention includes testing bovine nose fluids for total calcium levels, and correlating with the health of the cow. In certain types of tests later described, free calcium may be detected in bovine sweat fluids, (as opposed to total calcium). Further study on a limited data set indicates that the ionized fraction in nose sweat is a greater fraction of the total calcium than that for blood. The data generally indicates that the total calcium contains about 60-90% ionized calcium. Hence, nose sweat total calcium levels are more reflective of ionized calcium levels.

The nose fluid may be collected by a swab, an absorbent material such as a tissue or other cellulose fiber product or polymer materials, such as polymeric latex film, or collected in vial, for instance a thin pipette may be used, employing capillary action to draw the perspiration off the nose of a cow. Alternatively, the material employed to sample the sweat may be the test medium itself, such as a test strip later described. Any collection technique can be employed, provided the collecting medium does not contaminate the sample with extraneous calcium.

Once collected, the nose sweat must be tested for calcium levels. Any prior art tests for determining calcium levels in blood serum could be employed to determine the calcium levels in nose sweat, atomic absorption spectrophotometry analysis, fluorometric, titrimetric, flame photometry, ion selective electrodes and photometric determination, methods well known in the art. Collecting nose sweat is more readily accomplished than collecting blood samples, and there is no need to centrifuge the nose fluid sample, as must be done for a blood sample. Consequently, use of nose sweat as a surrogate for blood for the determination of calcium levels is an improvement in the state of the art.

Existing methods, however, still require testing the sample generally remote from the cow in question due to the need to undertake bichromatic measurements. A more efficient technique would be to employ a calcium determination method that could be used "cow-side." For instance, there are test strips used for determining calcium levels in fluids (primarily swimming pools) that could be used at cow-side. The strip itself could be used as the collection medium and test medium. Portions of the strips contain chemicals that respond to calcium, and the particular response is correlated to a reference table where the calcium concentration is correlated to the response. Generally, the response is a color change in the reacting chemical, the degree of color change is indicative of the calcium levels. Hash Company in Loveland Colo., Fisher Scientific, Pittsburgh, Pa., and a variety of other manufactures manufacture test strips used for determining calcium levels in water.

Proper use of such a strip requires an understanding of what the strip tests for, and to make sure the strip can test the calcium ranges desired. For instance, suppose a strip will only detect free calcium, (not that bound to proteins). Then the nose calcium levels reflected by the strip will be 60-90% of that determined by a traditional calcium test, and the disease correlation must be modified accordingly. To determine what a particular strip measures, check the manufacturer's information, or the strip can be field tested if necessary on suitable cows against another known standard to determine the appropriate readings. For instance, one optical test strip tests for calcium ions, and is described by Capitán-Vallvey, Ramos and de Cienfuegos-Gálvez, *Optical test strip for calcium determination based on a neutral ionophore*, Analytica Chimica Acta Volume 451, Issue 2, 25 Jan. 2002, Pages 231-241 Such a strip can be "calibrated" by comparing nose level readings to that of blood level determination of calcium.

One such strip is disclosed in WO/1996/004554 Urinary Test Strip for Determining Calcium Loss" (hereby incorporated by reference) which uses a latex pad impregnated or coated with a calcium sensitive dye, a dye fixer, a buffer and a possible magnesium binding agent. The Calcium sensitive dyes are MSTPM dyes such as: Alazarin Complexone, Eriochrome Blue, Cresolphthalein Complexone, Thymolphthalein Complexone (and the salts thereof, such as sodium salts) and other conventional complexing agents. To fix these dyes, common mordants to fix an acidic dye include salts of chromium, iron or aluminum or metallic mordants, more effective mordants take the form of polyelectrolytes and include polyvinylbenzyltrimethylammoniumchloride, polyvinylmβthylpyridine-chloride, polytrimethylaminoethylmethacrylatechloride, polytrimethylaminopropylamidomethacrylate, polydiallyldimethylammoniumchloride and polymonoallyltrimethylammoniumchloride, and dye binding with methylthymol blue and o-Cresolphthalein Complexone. Suitable buffers include Amino methyl Propanol, (AMP) or 3-(Cyclo hexylamino) 1 propane sulphonic acid (CAPS) and Sodium Borate. A requirement of the buffer is that the buffer does not bind Calcium ions in competition with the dye. The choice of buffer will be influenced partly by the particular dye used in the system and its optimal pH, but also by the need to select a high pH range at which Magnesium is not bound by the dye.

The buffer is used to maintain the pH of the reagent composition in a preferred range of about pH 10 to about pH 12. The tendency of the above dyes to bind Magnesium as well as Calcium is increased at lower pH levels of about 7 to about 8, but even then, the association constant is much greater for Calcium than for Magnesium. Complex formation with Magnesium progressively declines as the pH is raised from about 7 to about 12. However, the inclusion of a specific binding agent for Magnesium at any pH will minimize interference from this ion. Examples of suitable magnesium masking or binding agent are 8-Hydroxyquinoline or its-5-sulphonic acid salt or N-Benzoyl-N-Phenyl-Hydroxylamine other suitable complexing agents for Magnesium. See also, Tiez, *Fundamentals of Clinical Chemistry*, 1987 (W. B. Saunders) hereby incorporated by reference.

There are existing tests commercially available that can determine calcium levels, primarily for measuring "hardness" in water supplies or swimming pools. These tests are either strip based, or use a sample and use titration methods, searching for a color change. These tools can be also be used at cow side, suitably calibrated, with a sweat sample. For proper use, the collected sample, say a 1 cc nose sweat sample, may have to be mixed with a specific amount of distilled water (say 9 cc) to create a volume sufficient for testing. This additional fluid may be required for titration methods, or with strip methods. The resultant "hardness" readings would have to be adjusted accordingly to account for the added water volume.

However, some of these strips measure magnesium as well as calcium, and the inclusion of magnesium may skew readings higher that that for calcium alone (Mg is generally around 2.0-2.5 mg/dL for bovine blood serum samples) unless undertaken at a pH range where magnesium would not be complexed with the dye (or in the event that a magnesium binding agent is employed, such as 8-Hydroxyquinoline). One author has indicated that swimming pool hardness test kits can be used, with suitable calibration, to determine calcium levels in blood samples of cattle (but also indicated that such was not useful as the method still required a blood sample and the consequent centrifugation). Matsas D J, Warnick L D, Mechor G D, Seib L N, Fatone S, White M E, Guard C L. *Use of a water hardness test kit to measure serum calcium concentration in cattle. J Am Vet Med. Assoc.* 1999 Mar. 15; 214(6):826-8 hereby incorporated by reference.

A swab may simple be suitably coated or impregnated with a suitable color indicator at the desired marker range. For instance, other then the dyes mentioned previously, other dye agents which have been used for calcium detection include cresolphthalein, 1-amino-2-naphthol-4-sulfonic acid reagent, Folin-Denis reagent, 3-hydroxy-7-iodoquinoline-5-sulfonic acid reagent, Kisser's reagent; Loretin reagent, nickel nitrite reagent, pircrolonic acid reagent, potassium iodate reagent, or ricinoleate reagent, or those reagents disclosed in U.S. Pat. No. 5,948,632; 5,902,730; 5,747,345; 5,618,684; 5,482,866; 5,262,330; 5,057,435; or 4,795,712 (each hereby incorporated by reference).

I claim:

1. A method of diagnosing hypocalcemia in cattle including the steps of (a) collecting nose sweat from a cow; (b) testing said collected sweat for a calcium level, and (c) correlating said tested calcium level with the presence or absence of hypocalcemia.

2. The method of claim 1 where said calcium level comprises a dissociated calcium level.

3. The method of claim 1 where said calcium level comprises a total calcium level.

4. The method of claim 1 wherein said collection step is performed by using a collecting medium.

5. The method of claim 4 where said collecting medium comprises a cellulose fiber product or a polymer material product.

6. The method of claim 1 wherein said step of testing comprises testing said liquid sample using photometric determination methods.

7. The method of claim 1 wherein said step of testing said nose sweat for a calcium level is performed by said collecting medium.

8. The method of claim 7 wherein said collecting medium is a test strip having a color changing agent positioned thereon, said agent changing color in response to calcium levels is said collected sweat.

9. The method of claim 1 wherein said step of testing comprises testing said collected sample with a test strip having a color changing agent positioned thereon, said agent changing color in response to calcium levels is said collected sweat.

10. The method of claim 1 wherein said cow is a dairy cow.

11. The method of claim 1 wherein said tested calcium levels is correlated as a positive indicator for the presence of hypocalcemia when said tested calcium level indicates a level less than or equal to about 80 ppm calcium level.

12. The method of claim 1 wherein said tested calcium level is correlated as a positive indicator for hypocalcemia when said tested calcium level indicates a level less than or equal to about 70 ppm total calcium level.

13. The method of claim 8 wherein said color changing agent includes Alazarin Complexone, Eriochrome Blue, Cresolphthalein Complexone, or Thymolphthalein Complexone, or the salts thereof.

14. The method of claim 8 wherein said strip further includes a magnesium binding agent and a buffer.

15. The method of claim 1 wherein said calcium level is an ionized calcium level.

16. The method of claim 1 wherein said testing is performed at cow-side.

17. The method of claim 1 wherein said tested calcium levels is correlated as an indicator for the absence of hypocalcemia when said tested calcium level indicates a level greater than about 85 ppm total calcium level.

* * * * *